United States Patent [19]

Oine et al.

[11] Patent Number: 4,547,494

[45] Date of Patent: Oct. 15, 1985

[54] PYRROLIDOMOXINE CEPHALOSPORINS

[75] Inventors: Toyonari Oine, Nara; Yoshihisa Yamada, Kyoto; Mitsuyoshi Wagatsuma; Totaro Yamaguchi, both of Urawa; Satoshi Ohshima, Iwatsuki, all of Japan

[73] Assignee: Tanabe Seiyaku Co., Ltd., Osaka, Japan

[21] Appl. No.: 578,380

[22] Filed: Feb. 9, 1984

[30] Foreign Application Priority Data

Feb. 22, 1983 [JP] Japan ................................ 58-29063

[51] Int. Cl.[4] ........................................... C07D 501/60
[52] U.S. Cl. ...................................... 514/204; 546/27
[58] Field of Search ........................... 546/27; 424/246

[56] References Cited

U.S. PATENT DOCUMENTS 4,278,793 7/1981 Durckheimer ...................... 544/27

FOREIGN PATENT DOCUMENTS 2100734 1/1983 United Kingdom .

OTHER PUBLICATIONS

Ochiai, et al., "A New 1,3 Dipolar Cycloaddition Reaction", *Tetrahedron* 23; pp. 2641–2648 (1967).

*Primary Examiner*—Donald G. Daus
*Assistant Examiner*—G. Hendricks
*Attorney, Agent, or Firm*—Birch, Stewart, Kolasch & Birch

[57] ABSTRACT

A 7β-{(Z)-2-(2-aminothiazol-4-yl)-2-[(2-pyrrolidon-3-yl)oxyimino]acetamido}-3-(1-amino-1H-tetrazol-5-yl)thiomethyl-3-cephem-4-carboxylic acid or a pharmaceutically acceptable salt thereof is useful as an antimicrobial agent.

6 Claims, No Drawings

PYRROLIDOMOXINE CEPHALOSPORINS

This invention relates to a novel cephalosporin compound and a process for preparing same. More particularly, it relatees to 7β-{(Z)-2-(2-aminothiazol-4-yl)-2-[(2-pyrrolidon-3-yl)oxyimino]acetamido}-3-(1-amino-1H-tetrazol-5-yl)thiomethyl-3-cephem-4-carboxylic acid (I) or a pharmaceutically acceptable salt thereof. A pharmaceutical composition for use as an antimicrobial agent which comprises the cephalosporin compound (I) or a salt thereof as an active ingredient together with an inert carrier therefor is also provided in the present invention.

The new cephalosporin compound (I) of the present invention and a pharmaceutical salt thereof show potent antimicrobial activity against a wide variety of microorganisms including gram-positive and gram-negative bacteria and are useful as anti-bacterial agents, as nutritional supplements in animal food or as chemotherapeutic agents in warm-blooded animals, including man, in the treatment of infectious diseases caused by said gram-positive and gram-negative bacteria.

According to the present inventon, said cephalosporin compound, i.e., the compound of the formula:

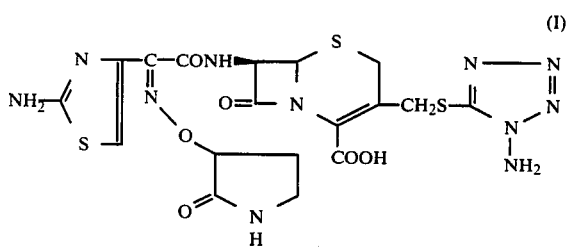

(I)

is prepared by the steps of:
(i) condensing a compound of the formula:

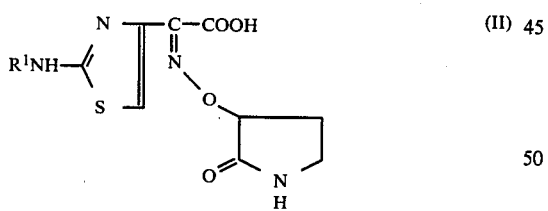

(II)

wherein $R^1NH$ is amino or a protected amino group, or a reactive derivative thereof with a compound of the formula:

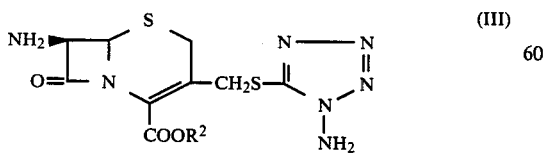

(III)

wherein $-COOR^2$ is carboxyl or a protected carboxyl group, or a salt thereof to give a compound of the formula:

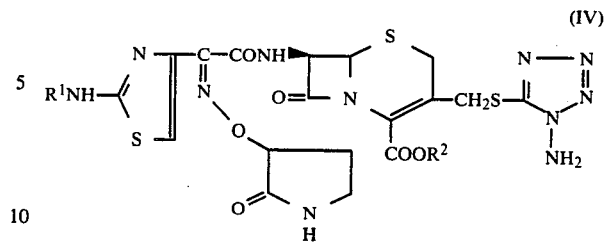

(IV)

wherein the symbols are the same as defined above, and
(ii) when $R^1NH$ is a protected amino group and/or $-COOR^2$ is a protected carboxyl group, further removing said protecting group(s) therefrom.

The structural formula (I) shown above intends to show that the isomeric configuration of the oxyimino group is Z (i.e., syn)-configuration. Although the Z (i.e., syn)-isomers of the invention are preferred and show the best biological properties, they may coexist with small amount of E (or anti)-isomer which may exist due to isomerization during the chemical preparation.

In the above-mentioned reaction, a wide variety of protecting groups which have been usually employed to protect amino group in the peptide synthesis can be used as the protecting group $R^1$. Examples of such protecting groups include lower alkanoyl such as formyl, acetyl and pivaloyl; mono-, di- or trihalogeno-lower alkanoyl such as chloroacetyl and trifluoroacetyl; lower alkoxycarbonyl such as methoxycarbonyl, ethoxycarbonyl and tert.-butoxycarbonyl; substituted or unsubstituted benzyloxycarbonyl such as benzyloxycarbonyl and p-methoxybenzyloxycarbonyl; substituted or unsubstituted phenyl-lower alkyl such as p-methoxybenzyl, benzyl and 3,4-dimethoxybenzyl; and di- or triphenyl lower alkyl such as benzhydryl and trityl. On the other hand, when $R^2$ in the compound (III) is a protecting group, the protecting group on the carboxyl group should be one which can be easily removed by conventional manners such as hydrolysis, acid treatment or reduction. Examples of such protecting group include lower alkyl such as methyl, ethyl or tert.-butyl; substituted or unsubstituted phenyl-lower alkyl such as benzyl, p-methoxybenzyl and p-nitrobenzyl; benzhydryl; tri-lower alkylsilyl such as trimethylsilyl; and the like. When $R^2$ is carboxyl, it is preferred that the compound (III) is converted to a salt thereof prior to carrying out the condensation reaction. Suitable examples of the salt of the compound (III) are inorganic salts such as sodium, potassium salts or organic amine salts such as trimethylamine, triethylamine salts. Moreover, while the compound (II) can exist in the form of two optical isomers due to the asymmetric carbon atom involved in the group of the formula:

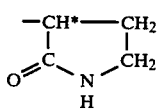

(wherein the asterisk denotes an asymmetric carbon atom), either an optical isomer of the compound (II) or a racemic modification thereof may be used for the purpose of the present invention.

The condensation reaction of the compound (II) or a reactive derivative thereof with the compound (III) or a salt thereof can be accomplished in conventional manners. For example, the condensation of the compound (II) in its free form with the compound (III) is conducted in the presence of a dehydrating agent in a solvent. Suitable examples of the dehydrating agent include dicyclohexylcarbodiimide, N-cyclohexyl-N'-morpholinocarbodiimide, N-ethyl-N'-(3-dimethylaminopropyl)carbodiimide, phosphorous oxychloride, phosphorous trichloride, thionyl chloride, oxalyl chloride, triphenylphosphine and the like. Vilsmeier reagent prepared from dimethylformamide and phosphorous oxychloride, from dimethylformamide and oxalyl chloride, from dimethylformamide and phosgene or from dimethylformamide and thionyl chloride may also be used as said dehydrating agent. It is preferred to carry out the reaction at a temperature of −50° to 50° C., especially at −30° to 20° C. Dioxane, tetrahydrofuran, acetonitrile, chloroform, methylene chloride, dimethylformamide, N,N-dimethylacetamide, ethyl acetate, pyridine, acetone and water are suitable as the solvent.

On the other hand, the condensation reaction of the reactive derivative of the compound (II) with the compound (III) or a salt thereof can be conducted either in the presence or absence of an acid acceptor in a solvent. Suitable examples of the reactive derivative of the compound (II) include the corresponding acid halides (e.g., chloride, bromide), mixed anhydrides (e.g., a mixed anhydride of the compound (II) with alkyl carbonate), active esters (e.g., p-nitrophenyl ester, 2,4-dinitrophenyl ester, succinimide ester, phthalimide ester, benzotriazole ester, 2-pyrrolidon-1-yl ester), acid azide and acid amides (e.g., imidazole amide, 4-substituted-imidazole amide, triazole amide). Dioxane, tetrahydrofuran, acetonitrile, chloroform, methylene chloride, dimethylformamide, N,N-dimethylacetamide, ethyl acetate, pyridine, acetone and water are suitable as the solvent. Moreover, suitable examples of the acid acceptor include alkali metal hydroxides (e.g., potassium hydroxide, sodium hydroxide), alkali metal carbonates or bicarbonates (e.g., sodium carbonate, sodium bicarbonate, potassium carbonate, potassium bicarbonate), trialkyl amines (e.g., trimethylamine, triethylamine), N,N-dialkylanilines (e.g., N,N-dimethylaniline, N,N-diethylaniline), pyridine and N-alkyl-morpholines (e.g., N-methylmorpholine). It is preferred to carry out the reaction at a temperature of −50° to 50° C., especially at −30° to 20° C.

The removal of the protecting group or groups from the compound (IV) thus obtained can be conducted by conventional manners such as, for example, hydrolysis, solvolysis, acid treatment or reduction. For example, when the protecting group $R^1$ is formyl, acetyl, tert.-butoxycarbonyl, benzhydryl or trityl and/or the protecting group $R^2$ is tert.-butyl or benzhydryl, said group or groups may be removed by treating the compound (IV) with an acid. Suitable examples of such acid include, for example, formic acid, trifluoroacetic acid, benzenesulfonic acid, p-toluenesulfonic acid, hydrochloric acid or hydrogen bromide, especially trifluoroacetic acid. This reaction may be conducted with or without a solvent. Examples of the solvent are water, methanol, ethanol, acetic acid or dioxane. It is preferred to carry out the reaction at a temperature of −30° to 70° C., especially at 0° to 30° C. Moreover, when the trifluoroacetic acid is used as the acid, it is preferred to carry it out in the presence of anisole. When the protecting group $R^1$ is benzyloxycarbonyl, p-methoxybenzyloxycarbonyl, benzyl, p-methoxybenzyl or 3,4-dimethoxybenzyl and/or the protecting group $R^2$ is benzyl, p-methoxybenzyl or p-nitrobenzyl, the removal of said protecting group or groups may be conducted by catalytic hydrogenation of the compound (IV) in hydrogen gas in the presence of a catalyst. This catalytic hydrogenation is preferably carried out at a temperature of 0° to 100° C., especially at 10° to 40° C., under atmospheric or increased pressure. Preferred examples of the catalyst include palladium-BaCO₃, palladium-charcoal and palladium black. Methanol, ethanol, tetrahydrofuran and water are suitable as the reaction solvent. Further, when the protecting group $R^1$ is trifluoroacetyl, pivaloyl, methoxycarbonyl or ethoxycarbonyl and/or the protecting group $R^2$ is methyl or ethyl, said group or groups may be removed by hydrolysis of the compound (IV). The hydrolysis of the compound (IV) can be carried out in conventional manners, for example, by treating it with an alkali agent such as sodium hydroxide or potassium hydroxide, or with an acid such as hydrochloric acid or hydrobromic acid. It is preferred to carry out said hydrolysis at a temperature of 0° to 70° C. especially at 10° to 30° C. When the protecting group $R^1$ is chloroacetyl, said group may be removed by treating the compound (IV) with thiourea in a solvent. Methanol, ethanol and water are suitable as the solvent. It is preferred to carry it out at a temperature of 20° to 80° C., especially at 40° to 80° C.

Concomitantly, the starting compound (II) of the invention is prepared, for example, by reacting a compound of the formula:

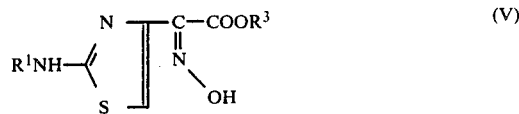

wherein $R^3$ is lower alkyl and $R^1NH$ is the same as defined above, with a 3-halogeno-2-pyrrolidone in the presence of an alkali agent (e.g., potassium carbonate) in a solvent (e.g., dimethylsulfoxide) at a temperature of 10° to 50° C. to give a compound of the formula:

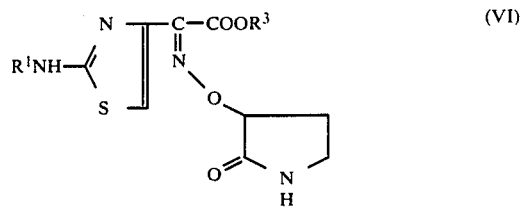

wherein $R^1NH$ and $R^3$ are the same as defined above, and then hydrolyzing the compound (VI). Alternatively, the starting compound (II) may be prepared by hydrolyzing the compound (V) to give a compound of the formula:

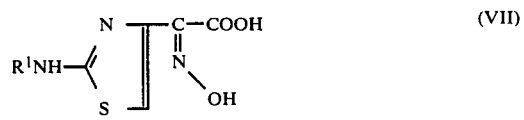

wherein $R^1NH$ is the same as defined above, and then reacting the compound (VII) with a 3-halogeno-2-pyrrolidone in the presence of an acid acceptor (e.g., sodium hydride) at a temperature of 10° to 40° C. in a solvent (e.g., dimethylsulfoxide). Moreover, as mentioned hereinbefore, the compound (II) involves two optical isomers due to the asymmetric carbon atom involved in the group of the formula:

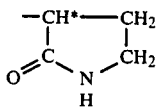

(wherein the asterisk denotes an asymmetric carbon atom). If required, however, such optical isomers may be separated from each other by optical resolution thereof. For example, the compound (II) in which $R^1$ is trityl can be readily separated into each optical isomers by reacting the racemic modification of the compound (II) with L- or D-phenylalanine methyl ester in a solvent (e.g., a mixture of methanol and dioxane) to form the diastereoisomeric salts thereof, and separating said diastereoisomers into each components thereof by selective crystallization. By said selective crystallization, the less soluble diastereoisomer is recovered as crystals from the reaction mixture and the more soluble diastereoisomer remains soluble therein. It is preferred to carry out said selective crystallization at a temperature of 10° to 40° C.

On the other hand, the starting compound (III) is prepared, for example, by reacting a compound of the formula:

NH$_2$—NH—CSS—R$^4$ (VIII)

wherein $R^4$ is lower alkyl, with an alkali metal azide (e.g., sodium azide) or a tetra-lower alkyl guanidium azide (e.g., tetramethylguanidium azide) in a solvent (e.g., methanol, ethanol, propanol, dimethylacetamide, formamide, water or a mixture thereof) at a temperature of 50° to 100° C. to give a compound of the formula:

and reacting the compound (IX) or a salt thereof (e.g., sodium, potassium, triethylamine, trimethylamine) with a compound of the formula:

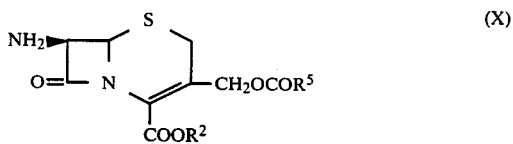

wherein $R^5$ is lower alkyl and —COOR$^2$ is the same as defined above, or a salt thereof (e.g., sodium, potassium, triethylamine, trimethylamine) at a temperature of 10° to 70° C., especially at 20° to 50° C., in the presence of a base (e.g., sodium carbonate, potassium carbonate, triethylamine) in an inert gas (e.g., nitrogen gas, argon gas) and in a solvent (e.g., a phosphate buffer (pH 6–7), acetonitrile, acetic acid, nitromethane). When the compound (IX) or (X) is used as the free form in this reaction, it is preferred to add methanesulfonic acid or boron trifluoride to the reaction solvent.

The cephalosporin compound (I) of the present invention and a pharmaceutically acceptable salt thereof show potent antimicrobial activity against a wide variety of microorganisms including those belonging to the genera Staphylococcus (e.g., S. aureus) and Pseudomonas (e.g., P. aeruginosa), and are particularly characterized by their potent antimicrobial activity against both gram-positive and gram-negative bacteria. Moreover, the cephalosporin compound (I) and a salt thereof show potent antimicrobial activity against bacteria belonging to the genera Klebsiella, Serratia, Citrobacter and Proteus. Further the cephalosporin compound (I) and a salt thereof are characterized in that they have a high stability against a variety of β-lactamases-producing microorganisms, especially against β-lactamases produced by Proteus vulgaris and Escherichia coli; and also that they are low in toxicity. For example, when sodium 7β-{(Z)-2-(2-aminothiazol-4-yl)-2-[((3S)-2-pyrrolidon-3-yl)oxyimino]acetamido}-3-(1-amino-1H-tetrazol-5-yl)thiomethyl-3-cephem-4-carboxylate was administered intravenously to mice at a dose of about 4 g/kg, no mice died during the period of 7 days after the administration.

The cephalosporin compound (I) of the present invention can be used for pharmaceutical use either in the free form or in the form of a salt thereof. Pharmaceutically acceptable salts of the compound (I) include, for example, non-toxic metalic salts such as sodium, potassium, calcium or aluminum salts; ammonium salt; salts thereof with non-toxic amines such as trialkylamines (e.g., triethylamine); salts thereof with inorganic acids such as hydrochloric acid or hydrobromic acid; salts thereof with organic acids such as oxalic acid or tartaric acid; and so forth. These salts are easily obtained by treating the compound (I) with a stoichiometrically equi-molar amount of the corresponding alkali agent or acid at around room temperature in an aqueous solvent. The cephalosporin compound (I) and a salt thereof can be administered either orally or parenterally (e.g., intravenously, intramuscularly, subcutaneously). The daily dose of the compound (I) or a salt thereof may vary over a wide range depending on the age, weight or conditions of patients, and the severity of diseases to be treated. In general, however, a preferred daily dose of said compound (I) or a salt thereof may be about 0.5 to about 10 g, especially 0.5 to 4.0 g, per body weight per day. Further, the compound (I) and a salt thereof may be used in the form of a pharmaceutical preparation containing the same compound in conjunction or admixture with pharmaceutical excipients suitable for oral or parenteral administration. Suitable excipients include, for example, gelatin, lactose, glucose, sodium chloride, starch, magnesium stearate, talcum, vegetable oil and other known medicinal excipients. The pharmaceutical preparations may be in solid form such as tablets, coated tablets, pills or capsules; or in liquid form such as solutions, suspensions or emulsions. They may be sterilized and/or may further contain auxiliaries such as stabilizing, wetting or emulsifying agent.

Practical and presently-preferred embodiments of the present invention are illustratively shown in the following Examples. Throughout the specification and claims, the term "lower alkyl" should be interpreted as referring to alkyl having one to four carbon atoms.

Experiment (Antimicrobial activity in vitro)

The minimum inhibitory concentration (MIC, μg/ml) of a test compound was determined by means of standard agar plate dilution method (based on the standard method of Japan Society of Chemotherapy). Media used in this experiments were Muller-Hinton agar (MHA: Nissui).

The results are shown in the following Table.

| Test compound Nos. | Chemical name |
|---|---|
| 1. | Sodium 7β-{(Z)-2-(2-aminothiazol)-4-yl)-2-[((3S)—2-pyrrolidon-3-yl)oxyimino]-acetamido}-3-(1-amino-1H—tetrazol-5-yl)-thiomethyl-3-cephem-4-carboxylate |
| 2. | Sodium 7β-{(Z)-2-(2-aminothiazol-4-yl)-2-[((3RS)—2-pyrrolidon-3-yl)oxyimino]-acetamido}-3-(1-amino-1H—tetrazol-5-yl)-thiomethyl-3-cephem-4-carboxylate |

TABLE

| Microorganisms tested | M.I.C. (μg/ml) Test compound Nos. | |
|---|---|---|
| | 1. | 2. |
| *Staphylococcus aureus* Terajima | 1.56 | 1.56 |
| *Escherichia coli* ML-1410 RGN-238 | 0.39 | 0.39 |
| *Klebsiella pneumoniae* | 0.2 | 0.2 |
| *Proteus vulgaris* | 0.1 | 0.2 |
| *Proteus vulgaris* GN76/C-1 | 0.39 | 0.39 |
| *Citrobacter freundii* | 0.1 | 0.2 |
| *Serratia marcescens* | 0.2 | 0.39 |
| *Pseudomonas aeruginosa* | 1.56 | 3.15 |

EXAMPLE 1

2.3 g of (Z)-2-(2-tritylaminothiazol-4-yl)-2-[((3S)-2-pyrrolidon-3-yl)oxyimino]acetic acid are dissolved in a mixture of 30 ml of tetrahydrofuran and 10 ml of N,N-dimethylacetamide, and 0.64 g of 1-hydroxybenzotriazole and 0.94 g of dicyclohexylcarbodiimide are added thereto under ice-cooling. The mixture is stirred at room temperature for 2 hours. The mixture is cooled with ice, and one g of 7β-amino-3-(1-amino-1H-tetrazol-5-yl)thiomethyl-3-cephem-4-carboxylic acid dissolved in a mixture of 10 ml of N,N-dimethylacetamide, 0.4 ml of water and 0.6 g of triethylamine is added thereto. The mixture is stirred at room temperature for 20 hours. The reaction mixture is poured into 75 ml of ice-water, and 25 ml of ethyl acetate are added thereto. The mixture is stirred for 10 minutes, and insoluble materials are filtered off. The aqueous layer is collected from the filtrate and is adjusted to pH 3 with 10% hydrochloric acid. The oily material thus obtained is extracted with a mixture of ethyl acetate and tetrahydrofuran (10:3). The extract is washed with water, dried and concentrated under reduced pressure to remove solvent. The residue is triturated with ethyl acetate and the thus-precipitated powder is collected by filtration. 7 ml of 80% aqueous formic acid are added to the powder (1.55 g), and the mixture is stirred at room temperature for one hour. 30 ml of water are added to the mixture, and insoluble materials are filtered off. The filtrate is concentrated to dryness under reduced pressure. Ether is added to the residue, and the resultant powder is collected by filtration. The powder is suspended in water, and an aqueous sodium bicarbonate solution is added thereto to dissolve said powder therein. The solution is introduced into a column packed with 140 ml of a non-toxic adsorption resin (manufactured by Mitsubishi Chemical Industries Ltd. under the trade name "Diaion HP-20"). After the column is washed with water, said column is eluted with 20% aqueous methanol. The eluate is concentrated to dryness under reduced pressure, acetone is added to the residue and the resultant precipitates are collected by filtration. 388 mg of sodium 7β-{(Z)-2-(2-aminothiazol-4-yl)-2-[((3S)-2-pyrrolidon-3-yl)oxyimino]acetamido}-3-(1-amino-1H-tetrazol-5-yl)thiomethyl-3-cephem-4-carboxylate are obtained as pale yellow powder. This product begins to decompose at around 230° C.

NMR (D$_2$O)δ: 2.0–2.8 (2H, m), 3.1–3.8 (4H, m), 4.07 (1H, d, J=13 Hz), 4.39 (1H, d, J=13 Hz), 5.03 (1H, t, J=7 Hz), 5.16 (1H, d, J=6 Hz), 5.71 (1H, d, J=6 Hz), 6.97 (1H, s)

EXAMPLE 2

1.15 g of (Z)-2-(2-tritylaminothiazol-4-yl)-2-[((3R)-2-pyrrolidon-3-yl)oxyimino]acetic acid are dissolved in a mixture of 15 ml of tetrahydrofuran and 5 ml of N,N-dimethylacetamide, and 0.32 g of 1-hydroxybenzotriazole and 0.47 g of dicyclohexylcarbodiimide are added thereto under ice-cooling and stirring. The mixture is stirred at the same temperature for 20 minutes and further at room temperature for 2 hours. The mixture is cooled with ice, and 0.5 g of 7β-amino-3-(1-amino-1H-tetrazol-5-yl)thiomethyl-3-cephem-4-carboxylic acid dissolved in a mixture of 5 ml of N,N-dimethylacetamide, 0.2 ml of water and 0.3 g of triethylamine is added thereto. The reaction mixture is treated in the same manner as described in Example 1. 242 mg of sodium 7β-{(Z)-2-(2-aminothiazol-4-yl)-2-[((3R)-2-pyrrolidon-3-yl)oxyimino]acetamido}-3-(1-amino-1H-tetrazol-5-yl)thiomethyl-3-cephem-4-carboxylate are obtained as colorless powder. This product begins to decompose at around 230° C.

NMR (D$_2$O)δ: 2.0–2.7 (2H, m), 3.2–3.8 (4H, m), 4.08 (1H, d, J=13 Hz), 4.40 (1H, d, J=13 Hz), 5.05 (1H, t, J=7 Hz), 5.16 (1H, d, J=5 Hz), 5.76 (1H, d, J=5 Hz), 7.00 (1H, s)

EXAMPLE 3

(1) 11.5 g of (Z)-2-(2-tritylaminothiazol-4-yl)-2-[((3RS)-2-pyrrolidon-3-yl)oxyimino]acetic acid are suspended in 150 ml of tetrahydrofuran, and 3.2 g of 1-hydroxybenzotriazole and 4.7 g of dicyclohexylcarbodiimide are added thereto under ice-cooling and stirring. The mixture is stirred at room temperature for 2 hours. The mixture is cooled with ice, and 4.9 g of 7β-amino-3-(1-amino-1H-tetrazol-5-yl)thiomethyl-3-cephem-4-carboxylic acid dissolved in a mixture of 50 ml of N,N-dimethylacetamide, 2 ml of water and 3 g of triethylamine are added thereto. The mixture is stirred at 5° to 10° C. for one hour and further at room temperature for 15 hours. The reaction mixture is poured into 750 ml of ice-water, and 250 ml of ethyl acetate are added thereto. The mixture is stirred for 10 minutes and insoluble materials are filtered off. The aqueous layer is collected from the filtrate and is adjusted to pH 3 with 10% hydrochloric acid. The oily material thus obtained is extracted with a mixture of ethyl acetate and tetrahydrofuran (10:3). The extract is washed with water, dried and concentrated under reduced pressure to remove solvent. The residue is triturated with ethyl acetate and thus-precipitated powder is collected by filtration. The powder is dissolved in 100 ml of tetrahydrofuran with heating, and 250 ml of ethyl acetate are added thereto. After cooling, crystalline precipitates are collected by filtration. 4.8 g of 7β-{(Z)-2-tritylaminothiazol-4-yl)-2-[((3RS)-2-pyrrolidon-3-yl)oxyimino]acetamido}-3-(1-amino-1H-tetrazol-5-yl)thiomethyl-3-cephem-4-carboxylic acid are obtained as colorless crystals.

NMR (DMSO-$d_6$)δ: 2.0–2.4 (2H, m), 3.0–3.4 (2H, m), 3.5–3.9 (2H, m), 4.1–4.5 (2H, m), 4.5–4.9 (1H, m), 5.0–5.3 (1H, m), 5.4–5.9 (1H, m), 6.7 (1H, s), 6.90 (2H, broad s), 7.0–7.7 (15H, m), 7.85 (1H, broad s), 8.6–8.9 (1H, m), 9.3–9.8 (1H, m)

(2) 4.8 g of 7β-{(Z)-2-tritylaminothiazol-4-yl)-2-[((3RS)-2-pyrrolidon-3-yl)oxyimino]acetamido}-3-(1-amino-1H-tetrazol-5-yl)thiomethyl-3-cephem-4-carboxylic acid are added to 22 ml of 80% aqueous formic acid, and the mixture is stirred at room temperature for one hour. 40 ml of water are added to the reaction mixture, and insoluble materials are filtered off. The filtrate is concentrated to dryness under reduced pressure. Ether is added to the residue, and the resultant powder is collected by filtration. The powder is treated in the same manner as described in Example 1. 1.9 g of sodium 7β-{(Z)-2-(2-aminothiazol-4-yl)-2-[((3RS)-2-pyrrolidon-3-yl)oxyimino]acetamido}-3-(1-amino-1H-tetrazol-5-yl)thiomethyl-3-cephem-4-carboxylate are obtained as pale yellow powder. This product begins to decompose at around 230° C.

NMR ($D_2O$)δ: 2.0–2.7 (2H, m), 3.2–3.8 (4H, m), 4.07 (1H, d, J=13 Hz), 4.39 (1H, d, J=13 Hz), 5.03 (1H, t, J=7 Hz), 5.16 (1H, d, J=5 Hz), 5.76 (1H, d, J=5 Hz), 7.02 (1H, s)

Preparation of Starting Compounds (1) 15.8 g of ethyl (Z)-2-(2-tritylaminothiazol-4-yl)-2-hydroxyiminoacetate are dissolved in 70 ml of dimethylsulfoxide, and 5.8 g of anhydrous potassium carbonate are added thereto. The mixture is stirred at room temperature for 20 minutes. 6.6 g of 3-bromo-2-pyrrolidone are added to said mixture, and the mixture is stirred at room temperature for 20 hours. The mixture is poured into 800 ml of water, and crystalline precipitates are collected by filtration and washed with water. The crystals are dissolved in chloroform, washed with water and then dried. Then, the chloroform solution is evaporated under reduced pressure to remove solvent. 100 ml of ethyl acetate are added to the residue, and allowed to stand at room temperature. Crystalline precipitates thus obtained are collected by filtration and dried. 16.0 g of ethyl (Z)-2-(2-tritylaminothiazol-4-yl)-2-[(2-pyrrolidon-3-yl)oxyimino]acetate are obtained.

M.p. 209°–210° C.

NMR (CDCl$_3$)δ: 1.30 (3H, t, J=7 Hz), 2.1–2.6 (2H, m), 3.1–3.6 (2H, m), 4.34 (2H, q, J=7 Hz), 4.90 (1H, t, J=7 Hz), 6.53 (1H, s), 7.0–7.6 (17H, m)

16.0 g of ethyl (Z)-2-(2-tritylaminothiazol-4-yl)-2-[(2-pyrrolidon-3-yl)oxyimino]acetate are added to a mixture of 160 ml of methanol and 30 ml of an aqueous 2N sodium hydroxide solution, and the mixture is refluxed for 30 minutes under heating. After cooling, crystalline precipitates are collected by filtration and washed with methanol. The crystals are suspended in 30 ml of water. Then, the suspension is adjusted to pH 3 with 2N hydrochloric acid. Crystalline precipitates are collected by filtration and dried. 11.4 g of (Z)-2-(2-tritylaminothiazol-4-yl)-2-[(2-pyrrolidon-3-yl)oxyimino]acetic acid are obtained.

M.p. 150°–153° C. (decomp.)

NMR (DMSO-$d_6$)δ: 1.8–2.4 (2H, m), 2.9–3.4 (2H, m), 4.63 (1H, t, J=7 Hz), 6.76 (1H, s), 6.9–7.6 (15H, m), 7.85 (1H, s), 8.70 (1H, broad s)

(2) 30 g of (Z)-2-(2-tritylaminothiazol-4-yl)-2-[(2-pyrrolidon-3-yl)oxyimino]acetic acid and 60 ml of methanol are added to 100 ml of dioxane containing 0.5 g of methyl L-phenylalaninate, and the mixture is heated at 50° C. to dissolve said acid therein. 700 ml of dioxane are added to the solution, and the mixture is stirred at room temperature for 5 hours. Crystalline precipitates are collected by filtration (the filtrate is hereinafter referred to as "Filtrate I"), and 14.3 g of the crude product thus obtained are dissolved in 24 ml of methanol. 280 ml of dioxane are added to the methanol solution. The mixture is stirred at room temperature for 4 hours, and crystalline precipitates are collected by filtration (the filtrate is hereinafter referred to as "Filtrate II"). 12.2 g of (Z)-2-(2-tritylaminothiazol-4-yl)-2-[((3S)-2-pyrrolidon-3-yl)oxyimino]acetic acid methyl L-phenylalaninate salt are obtained.

$[\alpha]_D^{25} -14.0°$ (C=1, methanol)

12.2 g of the above-mentioned salt are dissolved in 120 ml of methanol, and 176 ml of 0.1N hydrochloric acid are added thereto. The mixture is stirred for 2 hours under ice-cooling. Crystalline precipitates are collected by filtration and washed with methanol. 7.5 g of (Z)-(2-tritylaminothiazol-4-yl)-[((3S)-2-pyrrolidon-3-yl)oxyimino]acetic acid are obtained.

M.p. 142°–143° C. (decomp.)

$[\alpha]_D^{25} -38.8°$ (C=1, dimethylformamide)

(3) Filtrate I & II obtained in the above mentioned paragraph (2) are concentrated to dryness under reduced pressure. The residue is dissolved in 250 ml of methanol and then 450 ml of 0.1N hydrochloric acid are added dropwise to the solution. The mixture is stirred for 2 hours under ice-cooling. The resultant crystalline precipitates are collected by filtration, washed with methanol, and dried. 20 g of (Z)-2-(2-tritylaminothiazol-4-yl)-2-[(2-pyrrolidon-3-yl)oxyimino]acetic acid (containing an excess of the R-isomer) are obtained. 20.0 g of (Z)-2-(2-tritylaminothiazol-4-yl)-2-[(2-pyrrolidon-3-yl)oxyimino]acetic acid thus recovered and 40 ml of methanol are added to 70 ml of dioxane containing 7.0 g of methyl D-phenylalaninate, and the mixture is heated at 50° C. to dissolve said acid therein. 450 ml of dioxane are added to said solution. Then, the mixture is stirred at room temperature for 4 hours, and crystalline precipitates are collected by filtration. 13.3 g of the crude product thus obtained are dissolved in 20 ml of methanol, and 260 ml of dioxane are added thereto. The mixture is stirred at room temperature for 4 hours. Crystalline precipitates are collected by filtration. 12.0 g of (Z)-2-(2-tritylaminothiazol-4-yl)-2-[((3R)-2-pyrrolidon-3-yl)oxyimino]acetic acid methyl D-phenylalaninate salt are obtained.

$[\alpha]_D^{25} +13.9°$ (C=1, methanol)

12.0 g of the above-mentioned salt are dissolved in 120 ml of methanol, and 174 ml of 0.1N hydrochloric acid are added thereto. The mixture is stirred for 2 hours under ice-cooling. Crystalline precipitates are collected by filtration and washed with methanol. 7.3 g of (Z)-2-(2-tritylaminothiazol-4-yl)-2-[((3R)-2-pyrrolidon-3-yl)oxyimino]acetic acid are obtained.

M.p. 143°–144° C. (decomp.)

$[\alpha]_D^{25} +37.4°$ (C=1, dimethylformamide)

(4) 110 g of methyl dithiocarbazate and 60.4 g of 97% sodium azide are added to a mixture of 2 liters of ethanol and 0.4 liter of water, and the mixture is refluxed for 16 hours. After the reaction, the mixture is evaporated at 40° to 45° C. under reduced pressure to remove solvent. 500 ml of ethanol are added to the residue, and the resultant precipitates are collected by filtration. The precipitates are washed with ethanol and then dried, whereby 92 g of 1-amino-5-mercapto-1H-tetrazole sodium salt are obtained as a crude product. 11.22 g of said crude product are dissolved in 40 ml of water. 30 ml of 2N-sulfuric acid are added to said aqueous solution at 0° to 5° C., and the mixture was extracted continuously for 3 hours with 270 ml of ether. The extracts are combined and evaporated to remove solvent, and the residue obtained is recrystallized from a mixture of ethyl acetate and n-hexane. 4.3 g of 1-amino-5-mercapto-1H-tetrazole are obtained as colorless needles.

M.p. 162°–163° C. (decomp.)

IR$\nu_{max}^{nujol}$ (cm$^{-1}$): 3250, 3220, 3050, 1660, 1610

Mass (m/e): 117 (M$^+$, base peak), 74, 60, 43, 28

(5) 27.2 g of 7$\beta$-amino-cephalosporanic acid are added to an aqueous solution of sodium bicarbonate (sodium bicarbonate content: 9.24 g/liter) under stirring, 27.8 g of 1-amino-5-mercapto-1H-tetrazole sodium salt are added thereto. The mixture is stirred at 52°–53° C. in argon gas atmosphere for 3 hours. The mixture is treated with an activated charcoal and adjusted to pH 4.6 with 6 ml of methanesulfonic acid under cooling. The resultant precipitates are collected by filtration, washed with water and then dried. 17.3 g of 7$\beta$-amino-3-(1-amino-1H-tetrazol-5-yl)thiomethyl-3-cephem-4-carboxylic acid are obtained as ocherous powder.

M.p. 206° C. (decomp.)

IR$\nu_{max}^{nujol}$ (cm$^{-1}$): 3300, 3150, 1785, 1610, 1520, 1400, 1340, 1280, 1210

NMR (DMSO-d$_6$-CF$_3$COOD)$\delta$: 3.80 (2H, s, CH$_2$ at 2nd position), 4.40 (2H, d,d, J=5.4 and 13.5 Hz, CH$_2$ at C$^{3'}$), 5.20 (2H, s, H at 6th and 7th positions).

What we claim is:

1. A 7$\beta$-{(Z)-2-(2-aminothiazol-4-yl)-2-[(2-pyrrolidon-3-yl)oxyimino]acetamido}-5-(1-amino-1H-tetrazol-5-yl)thiomethyl-3-cephem-4-carboxylic acid or a pharmaceutically acceptable salt thereof.

2. The compound claimed in claim 1 which is 7$\beta$-{(Z)-2-(2-aminothiazol-4-yl)-2-[((3S)-2-pyrrolidon-3-yl)oxyimino]acetamido}-3-(1-amino-1H-tetrazol-5-yl)thiomethyl-3-cephem-4-carboxylic acid or a pharmaceutically acceptable salt thereof.

3. A pharmaceutical composition which comprises an antimicrobial effective amount of a cephalosporin compound 7$\beta$-{(Z)-2-(2-aminothiazol-4-yl)-2-[(2-pyrrolidon-3-yl)oxyimino]acetamido}-3-(1-amino-1H-tetrazol-5-yl)thiomethyl)-3-cephem-4-carboxylic acid or a pharmaceutically acceptable salt thereof and a pharmaceutically acceptable carrier therefor.

4. The pharmaceutical composition claimed in claim 3, wherein said cephalosporin compound is 7$\beta$-{(Z)-2-(2-aminothiazol-4-yl)-2-[((3S)-2-pyrrolidon-3-yl)oxyimino]acetamido}-3-(1-amino-1H-tetrazol-5-yl)thiomethyl-3-cephem-4-carboxylic acid or a pharmaceutically acceptable salt thereof.

5. A method of treating microbial infections in a warm-blooded animal comprising administering to said warm-blooded animal an antimicrobial effective amount of a cephalosporin compound 7$\beta$-{(Z)-2-(2-aminothiazol-4-yl)-2-[(2-pyrrolidon-3-yl)oxyimino]acetamido}-3-(1-amino-1H-tetrazol-5-yl)thiomethyl-3-cephem-4-carboxylic acid or a pharmaceutically acceptable salt thereof.

6. The method claimed in claim 5, wherein said cephalosporin compound is 7$\beta$-{(Z)-2-(2-aminothiazol-4-yl)-2-[((3S)-2-pyrrolidon-3-yl)oxyimino]acetamido}-3-(1-amino-1H-tetrazol-5-yl)thiomethyl-3-cephem-4-carboxylic acid or a pharmaceutically acceptable salt thereof.

* * * * *